United States Patent [19]

Ogata

[11] Patent Number: 4,459,412
[45] Date of Patent: Jul. 10, 1984

[54] 1-BENZYLIMIDAZOLE DERIVATIVES

[75] Inventor: Masaru Ogata, Hyogo, Japan

[73] Assignee: Shionogi & Co., Ltd., Osaka, Japan

[21] Appl. No.: 516,431

[22] Filed: Jul. 25, 1983

Related U.S. Application Data

[63] Continuation of Ser. No. 327,463, Dec. 4, 1981, abandoned.

[30] Foreign Application Priority Data

Dec. 5, 1980 [JP] Japan ................................. 55/172329

[51] Int. Cl.³ .................. C07D 233/60; C07D 233/62
[52] U.S. Cl. ...................................... 548/335; 548/336
[58] Field of Search ............... 548/335, 336, 341, 203, 548/202, 204

[56] References Cited

U.S. PATENT DOCUMENTS 4,328,348  5/1982  Ogata ................................... 548/336

*Primary Examiner*—Robert W. Ramsuer
*Attorney, Agent, or Firm*—Birch, Stewart, Kolasch & Birch

[57] ABSTRACT

1-Benzylimidazole derivatives useful as antimycotic agents having superior activity and as agricultural bactericides effective against various plant pathogenic bacteria and soil bacteria, derived from hydroxyphenyl-vinylimidazoles.

3 Claims, No Drawings

1-BENZYLIMIDAZOLE DERIVATIVES

This application is a continuation of application Ser. No. 327,463 filed on Dec. 4, 1981 now abandoned.

BACKGROUND OF THE INVENTION

Benzylimidazole derivatives have been found to be useful as antimycotic agents or as agricultural bactericides and there are many patents relating thereto (e.g., British Pat. Nos. 1,510,016, 1,469,617, 1,305,863, 1,304,623, 1,298,535, 1,288,196, 1,268,745, 1,268,690, 1,264,958, 1,263,850, 1,260,588, 1,256,476, and 1,170,188). Above all "clotrimazole" (Bayer) has been well known as an antimycotic agent.

The present inventors have investigated intensively to find superior antimycotic agents and have improved the know compounds as described in British Pat. No. 2,054,560 (U.S. Pat. No. 4,328,348), to find the new compounds of the present invention.

BRIEF SUMMARY OF THE INVENTION

The present invention relates to compounds of the general formula:

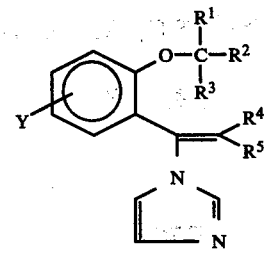

(I)

wherein
- Y is hydrogen, halogen, trifluoromethyl, $C_1$-$C_5$ alkyl, $C_1$-$C_5$ alkoxy, $C_2$-$C_5$ alkoxycarbonyl, carbamoyl, nitro, or optionally substituted $C_1$-$C_{10}$ acyl;
- $R^1$ and $R^2$ each is $C_1$-$C_5$ alkyl, $C_1$-$C_5$ alkoxy, $C_2$-$C_5$ alkoxyalkyl, optionally substituted $C_6$-$C_{10}$ aryl, optionally substituted $C_7$-$C_{12}$ aralkyl, or optionally substituted 5- or 6-membered heterocyclic residue;
- $R^1$ and $R^2$, taken together with the adjacent carbon, may form a $C_6$-$C_{10}$ carbocyclic residue;
- $R^3$ is hydrogen, $C_1$-$C_5$ alkyl, or $C_6$-$C_{10}$ aryl; and
- $R^4$ and $R^5$ each is hydrogen, $C_1$-$C_5$ alkyl, $C_7$-$C_{12}$ aralkyl, or $C_6$-$C_{10}$ aryl and the pharmaceutically acceptable acid addition salts thereof, wherein the substituents include $C_1$-$C_5$ alkyl, $C_2$-$C_5$ alkoxycarbonyl, $C_1$-$C_5$ alkoxy, or halogen.

The present invention is intended to provide 1-benzylimidazole derivatives (I) useful as antimycotic agents for human or animal use, or as agricultural bactericides.

DETAILED EXPLANATION

The terms employed in the above definitions are shown practically as follows:
- Halogen is fluorine, chlorine, bromine, or iodine;
- $C_1$-$C_5$ alkyl is methyl, ethyl, propyl, isopropyl, butyl, isobutyl, or pentyl;
- $C_1$-$C_5$ alkoxy is methoxy, ethoxy, propoxy, isopropoxy, butoxy, isobutoxy, or pentyloxy;
- $C_2$-$C_5$ alkoxycarbonyl is methoxycarbonyl, ethoxycarbonyl, or propoxycarbonyl;
- $C_1$-$C_{10}$ acyl is alkanoyl such as acetyl, propionyl, and butyryl or aroyl such as benzoyl;
- $C_2$-$C_5$ alkoxyalkyl is methoxyethyl, ethoxypropyl, propoxyethyl, or butoxymethyl;
- $C_6$-$C_{10}$ aryl is phenyl or naphthyl;
- $C_7$-$C_{12}$ aralkyl is benzyl, phenethyl, phenylpropyl, or phenylbutyl;
- 5- or 6-membered heterocyclic residue is pyridyl, furyl, thienyl, oxazolyl, isoxazolyl, or thiazolyl; and
- the $C_6$-$C_{10}$ carbocyclic residue that $R^1$ and $R^2$, taken together, form is cyclohexyl or tetralinyl.

The objective compounds (I) can be produced by the method shown in the following scheme:

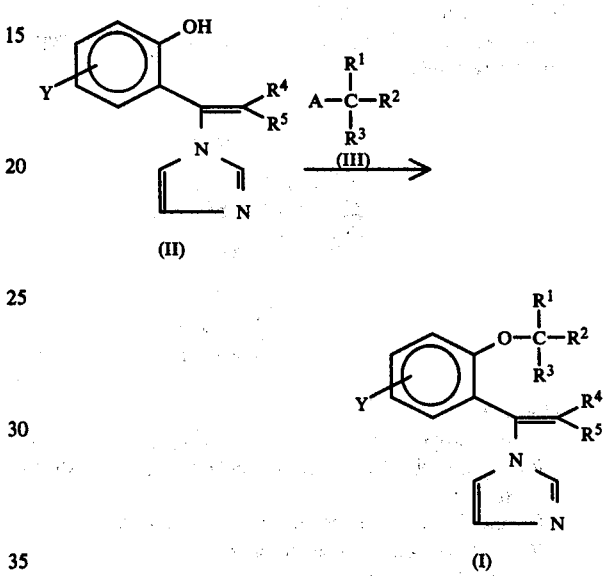

wherein A is a reactive group (e.g., halogen, tosyloxy, etc.) and $R^1$, $R^2$, $R^3$, $R^4$, $R^5$, and Y have the same meanings as described above.)

This reaction is carried out by reaction of phenols (II) with reaction reagents (III) in the presence of a base. The base is, for example, an inorganic or organic base such as sodium hydroxide, sodium hydride, sodium amide, sodium ethoxide, triethylamine, and pyridine. This reaction is carried out in the presence of a proper inert solvent (e.g., benzene, methanol, methylene chloride, chloroform, tetrahydrofuran, dimethylformamide, dimethylsulfoxide, etc.) at room temperature or under cooling or heating at a temperature of, for example, approximately 0°–150° C.

The starting phenols (II) are obtained, for example, by reaction of the corresponding ketones (IV) with N,N'-thionyldiimidazole or N,N'-carbonyldiimidazole:

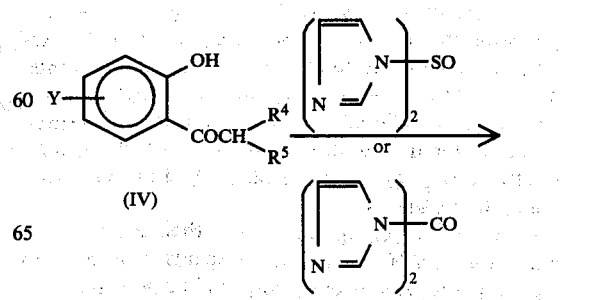

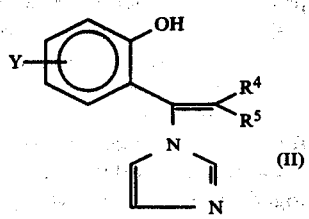

(II)

wherein R⁴, R⁵, and Y have the same meanings as described above (reference: Jap. Pat. Appln. No. 54-71953; ibid. 115465).

A preferable compound of this invention is represented by the formula:

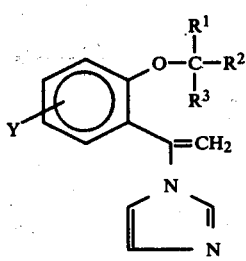

wherein
- $R^1$ is methyl, ethyl, propyl, or phenyl,
- $R^2$ is phenyl, chlorophenyl, methoxyphenyl, or thienyl, or
- $R^1$ and $R^2$, taken together, form tetralinyl;
- $R^3$ is hydrogen or phenyl; and
- Y is hydrogen or chlorine.

The thus prepared objective compounds (I) can be changed into the pharmaceutically acceptable acid addition salts. Acids which form such salts are, for example, organic acids such as acetic acid, citric acid, tartaric acid, malic acid, succinic acid, oxalic acid, maleic acid, fumaric acid, and methanesulfonic acid, or inorganic acids such as hydrohalogenic acid, sulfonic acid, nitric acid, and phosphoric acid.

The objective compounds (I) or their salts having superior antimycotic activity are useful as drugs for human and animal use. For example, the minimum inhibitory concentrations (MIC) of 1-[1-[2-(4-chloro-α-methylbenzyloxy)phenyl]vinyl]imidazole.oxalate in in vitro antimicrobial tests were found to be 3.2, 6.2, and 0.1 (γ/ml) against *Candida albicans* M-9, *Aspergillus fumigatus*, and *Trichophyton asteroides*, respectively.

The objective compounds (I) or their acid addition salts solely or together with additives such as excipients, diluents, and dispersing agents may be formulated into the preparations for external or internal use. Such dosage forms are, for example, solutions, suspensions, powders, granules, capsules, tablets, injections, ointments, tinctures, and suppositories, which can usually be prepared by conventional means in formulation. They may be administered to adult humans at a dose of, for example, 100-2000 mg/day, preferably 200-1000 mg/day, in oral administrations.

The objective compounds (I) or their acid addition salts show antimicrobial activity against various kinds of plant pathogenic bacteria and soil bacteria and so are useful as antimicrobials for agricultural use.

The objective compounds (I) or their acid addition salts show superior preventive activity against the following plant pathogenic bacteria.

| | |
|---|---|
| Rice plant: | blast, brown spot, damping off |
| Wheat and barley: | stem rust, loose smut, powdery mildew |
| Pear: | red spot, black rot, black spot |
| Grape: | gray mold, ripe spot, downy mildew, leaf spot, white rot |
| Apple: | Alternaria leaf spot, canker, black spot, red spot, blossom blight |
| Peach: | gray spot |
| Cucumber: | downy mildew, powdery mildew, anthracnose, clerotinia rot, other soil bacterial diseases |
| Pimento: | powdery mildew |
| Tobacco: | red spot, powdery mildew |

The objective compounds (I) or their acid addition salts solely or together with additives and carriers which are usually used for agricultural bactericides, are formulated into, for example, wettable powder, granules, dust, emulsions, tablets, aerosol, fumigants, oils, etc., and applied. The appropriate amount to be applied is approximately 0.5-100 g (as effective ingredient) per are.

The examples of the present invention are shown as follows.

EXAMPLE 1

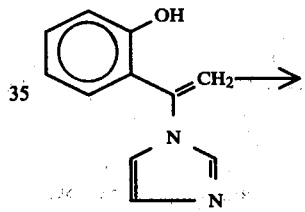

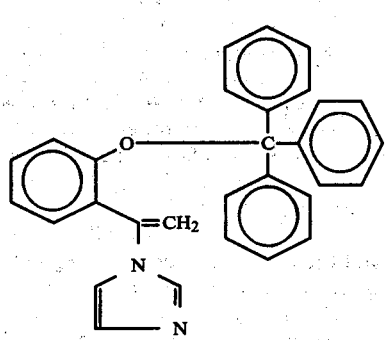

To a suspension of 1-[1-(2-hydroxyphenyl)vinyl]imidazole (500 mg) and triethylamine (407 mg) in dry methylene chloride (5 ml) is added trityl chloride (1.12 g) under stirring at room temperature, and the mixture is stirred at room temperature for 1 hour. To the mixture ice water is added and extracted with methylene chloride. The methylene chloride extract is dried on anhydrous sodium sulfate, and then concentrated. The residue is chromatographed on a column of silica gel, and eluted with methylene chloride-methanol (3-5%). The eluate is concentrated and the residue is crystallized from isopropyl ether and a small amount of petroleum ether to give 1-[1-(2-trityloxyphenyl)vinyl]imidazole (525 mg). mp. 149°-144° C.

Elementary analysis (for $C_{30}H_{24}N_2O$) Calcd. C, 84.05; H, 5.65; N, 6.54. Found. C, 84.36; H, 5.70; N, 6.52.

EXAMPLE 2

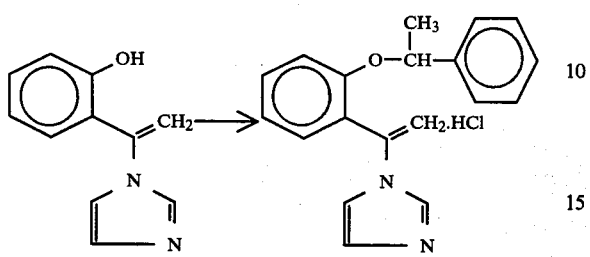

To a solution of 1-[1-(2-hydroxyphenyl)vinyl]imidazole (1.0 g) in dry dimethylformamide (10 ml) is added a suspension (310 mg) of sodium hydride (50%) in mineral oil under stirring and ice-cooling, and the mixture is stirred under ice-cooling for 5 minutes. α-Methylbenzyl bromide (1.19 g) is added thereto and stirred at room temperature for 30 minutes. Ice-water is added to the reaction solution and extracted with ether. The ether extract is washed with water, dried on anhydrous sodium sulfate, and then concentrated. The residue is chromatographed on a column of silica gel and eluted with methanol-methylene chloride (2%). The eluate is concentrated, hydrochloric acid/ethanol is added to the residue, and ether is distilled off. The residue is washed with ether and the precipitates are collected by filtration and recrystallized from acetonitrile-ethyl acetate to give 1-[1-[2-(α-methylbenzyloxy)phenyl]vinyl]imidazole.hydrochloride (1.05 g). mp. 172.5°–174.5° C.

Elemental analysis (for $C_{19}H_{18}N_2O \cdot HCl$) Calcd. C, 69.83; H, 5.86; N, 8.57; Cl, 10.85. Found. C, 70.00; H, 5.84; N, 8.83; Cl, 11.02.

EXAMPLES 3–14

The following starting compounds (II) and (III) are employed in the reaction and the reaction is carried out in the same manner as in Example 1 to give the objective compounds (I):

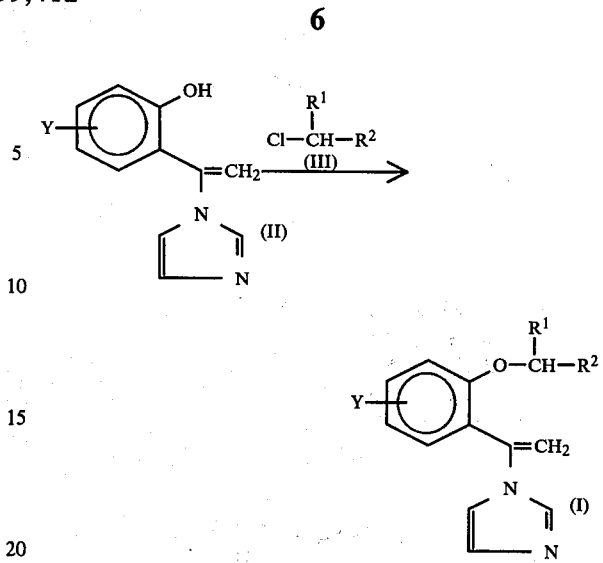

| Example No. | Y | $R^1$ | $R^2$ | mp. (°C.)/ IR (cm$^{-1}$) | Salt |
|---|---|---|---|---|---|
| 3 | 5-Cl | Me | Ph | 74–75 | HCl |
| 4 | H | Et | Ph | 130–132 | (COOH)$_2$ |
| 5 | 5-Cl | Et | Ph | 1635 (film) | — |
| 6 | H | Me | 4-Cl—Ph | 120–121 | (COOH)$_2$ |
| 7 | H | Me | 4-MeO—Ph | 1633 (film) | — |
| 8 | H | Pr | Ph | 105–107 | (COOH)$_2$ |
| 9 | 5-Cl | Pr | Ph | 1632 (film) | — |
| 10 | H | Me | 3-Cl—Ph | 97–98 | (COOH)$_2$ |
| 11 | 5-Cl | Me | 3-Cl—Ph | 115–117 | (COOH)$_2$ |
| 12 | 5-Cl | Me | 4-Cl—Ph | 179.5–180 | HCl |
| 13 | 5-Cl | Me | (thienyl)* | 1635 (film) | — |
| 14 | H | (tetralinyl)* | | 136.5 (d) | (COOH)$_2$ |

Notes
(1) The abbreviations of the formula have the following meanings:
Me: methyl; Et: ethyl; Pr: propyl; Ph: phenyl; d: decomposition; MeO: methoxy
(2) * is a example in which $R^1$ and $R^2$, taken together with the adjacent carbon, form a carbocyclic residue.

What is claimed is:
1. A compound selected from the group consisting of 1-[1-(2-trityloxyphenyl)vinyl]imidazole and 1-[1-(2-(1-tetralinyloxy)phenyl)vinyl]imidazole.
2. Compound according to claim 1, which is 1-[1-(2-trityloxyphenyl)vinyl]imidazole.
3. Compound according to claim 1, which is 1-[1-(2-(1-tetralinyloxy)phenyl)vinyl]imidazole.

* * * * *